United States Patent
Ascêncio et al.

(10) Patent No.: US 11,459,350 B2
(45) Date of Patent: Oct. 4, 2022

(54) PROCESS FOR PRODUCING MONOSACCHARIDES FROM CHITIN AND/OR CHITOSAN BY MEANS OF CHEMICAL AND/OR ENZYMATIC HYDROLYSIS AND THE USES THEREOF

(71) Applicants: INSTITUTO FEDERAL DE EDUCAÇÃO, CIÊNCIA E TECNOLOGIA DO TOCANTINS—IFTO, Palmas (BR); FUNDAÇÃO UNIVERSIDADE FEDERAL DO TOCANTINS—UFT, Palmas (BR)

(72) Inventors: Sérgio Donizeti Ascêncio, Palmas (BR); Adão Lincon Bezerra Montel, Palmas (BR); Éber Eurípedes de Souza, Palmas (BR)

(73) Assignees: INSTITUTO FEDERAL DE EDUCAÇÃO, CIÊNCIA E TECNOLOGIA DO TOCANTINS—IFTO; FUNDAÇÃO UNIVERSIDADE FEDERAL DO TOCANTINS—UFT

( * ) Notice: Subject to any disclaimer, the term of this patent is extended or adjusted under 35 U.S.C. 154(b) by 31 days.

(21) Appl. No.: 16/310,303

(22) PCT Filed: Jun. 22, 2017

(86) PCT No.: PCT/BR2017/050160
§ 371 (c)(1),
(2) Date: Dec. 14, 2018

(87) PCT Pub. No.: WO2017/219110
PCT Pub. Date: Dec. 28, 2017

(65) Prior Publication Data
US 2019/0256540 A1 Aug. 22, 2019

(30) Foreign Application Priority Data
Jun. 22, 2016 (BR) .................. 102016014767-0

(51) Int. Cl.
| | |
|---|---|
| *C07H 3/02* | (2006.01) |
| *C12P 19/02* | (2006.01) |
| *C12P 19/14* | (2006.01) |
| *C07H 13/04* | (2006.01) |
| *C07H 5/06* | (2006.01) |
| *C13K 13/00* | (2006.01) |
| *C07H 1/08* | (2006.01) |

(52) U.S. Cl.
CPC .................. *C07H 3/02* (2013.01); *C07H 1/08* (2013.01); *C07H 5/06* (2013.01); *C07H 13/04* (2013.01); *C12P 19/02* (2013.01); *C12P 19/14* (2013.01); *C13K 13/00* (2013.01)

(58) Field of Classification Search
CPC ... C07H 3/02; C07H 1/08; C07H 5/06; C07H 13/04; C12P 19/02; C12P 19/14; C12K 13/00
USPC ............................................................ 435/99
See application file for complete search history.

(56) References Cited

U.S. PATENT DOCUMENTS

| | | | |
|---|---|---|---|
| 3,922,260 A | 11/1975 | Peniston et al. | .......... 260/211 R |
| 5,137,818 A * | 8/1992 | Harder | .................. C12N 11/04 |
| | | | 435/177 |
| 5,312,908 A * | 5/1994 | Nakao | ...................... C07H 3/10 |
| | | | 536/20 |

OTHER PUBLICATIONS

International Preliminary Report on Patentability issued in application No. PCT/BR2017/050160, dated Dec. 18, 2018 (15 pgs).

(Continued)

*Primary Examiner* — Jennifer M. H. Tichy
(74) *Attorney, Agent, or Firm* — Hayes Soloway P.C.

(57) ABSTRACT

Disclosed is a process for obtaining monosaccharides in acid aqueous solution from chitin or chitosan by means of chemical and/or enzymatic hydrolysis. By using low-cost and easily obtainable reagents, this process makes it possible to obtain sugar solutions of industrial importance. With our new production process to supply the food industry and/or the chemicals industry, manufacturing of monosaccharides is less complex and thus technically and financially more viable.

16 Claims, 1 Drawing Sheet

(56) References Cited

OTHER PUBLICATIONS

International Search Report and Written Opinion issued in application No. PCT/BR2017/050160, dated Aug. 22, 2017 (18 pgs).
Jung et al., Bioproduction of Chitooligosaccharides: Present and Perspectives, Mar. Drugs 2014, 12, 5328-5356 (29 pgs).
Knight et al., Structure, depolymerization, and cytocompatibility evaluation of glycol chitosan, Journal of Biomedical Materials Research Part A, 2007 (12 pgs).
Pan et al., Preparation of glucosamine by hydrolysis of chitosan with commercial α-amylase and glucoamylase, J Zhejiang Univ-Sci B (Biomed and Biotechnol) 2011 12(11):931-934 (4 pgs).
Rege et al., Chitosan processing: influence of process parameters during acidic and alkaline hydrolysis and effect of the processing sequence on the resultant chitosan's properties, Carbohydrate Research 321 (1999) 235-245 (11 pgs).
Salim et al., Chitooligosaccharide-2,5-anhydro-D-mannonic Acid, Molbank, 2014, M832 (4 pgs).
Tømmeraas et al., Preparation and characterisation ofoligosaccharides produced by nitrous acid depolymerisation of chitosans, Carbohydrate Research 333 (2001) 137-144 (8 pgs).
Vårum et al., Acid hydrolysis of chitosans, Carbohydrate Polymers 46 (2001) 89-98 (10 pgs).
Waksmundzka-Hajnos et al., Thin Layer Chromatography in Phytochemistry, 2008, book summary only (2 pgs).
Ascencio, S. D., Extraction, quantification and chemical characterization of low molecular mass carbohydrates of red algae (*Rhodophyta*). Curitiba, 2002. Dissertation (Master in Biochemistry)—Biological Sciences, Federal University of Paraná, 2002 (130 pgs).

\* cited by examiner

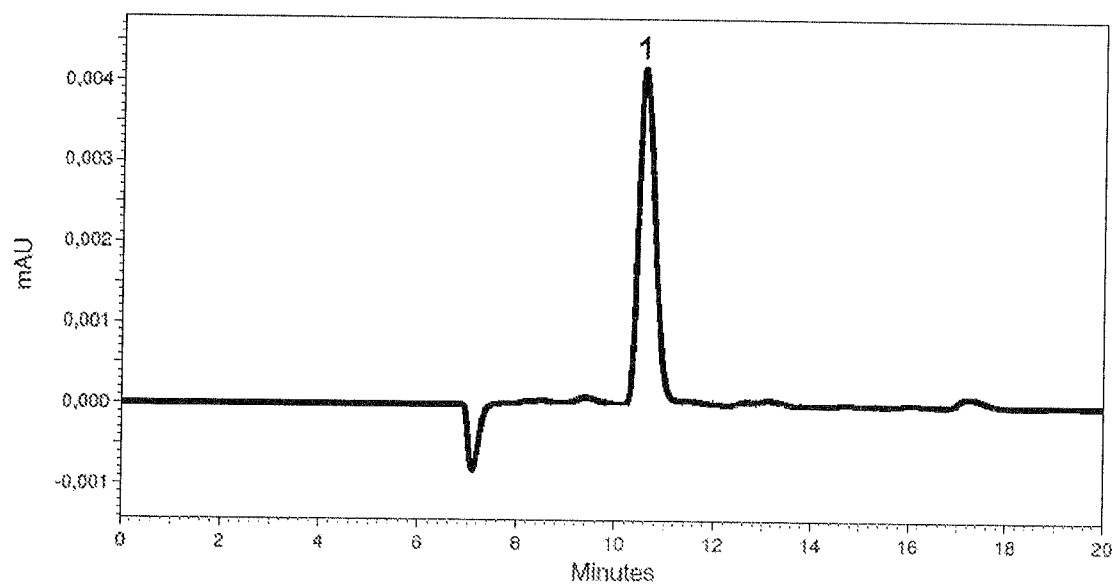

PROCESS FOR PRODUCING MONOSACCHARIDES FROM CHITIN AND/OR CHITOSAN BY MEANS OF CHEMICAL AND/OR ENZYMATIC HYDROLYSIS AND THE USES THEREOF

FIELD OF THE INVENTION

The present invention discloses a process for obtaining monosaccharides from chitin or chitosan in acid aqueous solution. The process makes it possible to obtain a solution of hexoses using low cost and of easily obtainable reagents. The technical field to which this invention is related aims to provide, by means of an innovative process of production in food industry and/or chemical industry, an alternative method for producing sugars which is technically and economically more viable.

BACKGROUND OF THE INVENTION

The production of second-generation ethanol is strongly dependent on the efficiency in obtaining fermentable monosaccharides from biomass. Methods traditionally used resort to chemical and/or enzymatic hydrolysis of lignocellulose, the most abundant source of biomass. The major problems associated to ethanol from lignocellulosic biomass derive from the refractory structure of lignocellulose, which requires a process of delignification of biomass (the lignin present in the biomass interferes with the activity of the cellulase enzymes used) and the fermentation of the pentoses produced in the process (such as xylose and arabinose, which are not fermentable by most organisms used to produce ethanol, among them yeasts of genus *Saccharomyces*). An alternative approach investigated to produce second-generation ethanol uses chitin. Chitin, the natural poly-N-acetyl-glucosamine polysaccharide, is a structural component of crustaceans, insects, fungi and other chitinous sources, and it is the second most abundant biopolymer in nature, only behind cellulose. It is estimated that 1 to 100 billion tonnes of chitinous waste is annually produced around the globe, mainly from the fishing industry. The hydrolysis of chitin causes its deacetylation and produces chitosan, a polymer whose monomeric unit is glucosamine. The process of chitosan production from chitin by acid or basic hydrolysis is influenced by several factors, such as temperature and reaction time, as observed by REGE, P. R. and BLOCK, L. H. (1999) in an article published in the journal Carbohydrate Research, volume 321.

Obtaining sugars from chitosan made by the chitosan depolymerization reaction both by enzymatic and chemical pathways has been studied by several authors. Pan S. K. et al. (2011) were able to produce glucosamine (an amino sugar) from chitosan by using commercial alpha-amylases and glucoamylases. Nitrous acid (HNO2) was highly investigated for chitosan depolymerization. This acid is able to react with amines, producing nitrogen gas (N2) and water. Due to the amino group (—NH2) present in the monomer, chitosan is especially susceptible to this reaction.

Using a combination of acetic acid (2.5%) and mild conditions (temperature of 4° C., reaction time of 24 h, dark environment and concentrations of 1.5 mmol of NaNO2), Tømmeraas et al. (2001), in an article published in the journal Carbohydrate Research, volume 333, were able to obtain oligomers with a chain having a monomer with the 2,5-D-mannose structure in its end, but were not able to obtain the monomer (sugar).

By using more vigorous conditions (room temperature, reaction time of 24 h, concentrations of 0.66 M of NaNO2 and concentrated HCl—37%), Salim et al. (2014) were able to produce oligomers with the terminal chain 2,5-D-manofuranoside.

A detailed study of the deacetylation and depolymerization mechanisms conducted by Knight et al. (2007) in an article published in the Journal of Biomedical Materials Research, volume 83A, using NaNO2 in dilute concentrations and different pH values (1.6, 2.9 and 5.1) demonstrated that pH affects the product of the reaction in a determinant way, and at very low pH values, N-nitrosamines are formed.

In another study conducted by Valum et al. (2001) published in the journal Carbohydrate Research, volume 46, it has been shown that, in a medium comprising concentrated HCl, the depolymerization reaction of the glucosidic bond in partially acetylated chitosan is 10 times faster than the deacetylation reaction while, in diluted acid, the two reactions occur at equal speeds.

U.S. Pat. No. 3,922,260 (PENISTON, Q. P.; JOHNSON, E. L. Process for depolymerization of chitosan—U.S. Pat. No. 3,922,260, filed Nov. 25, 1975) explain the discovery of a process for obtaining short chain reducing molecules using the dissolution of chitosan in diluted acetic acid and diluted solution of sodium nitrite (with concentrations in order of 0.124 mol/L).

In the present invention, it relates to the discovery of combinations of temperature and nitrous acid concentration conditions which enable the hydrolysis of chitosan and/or chitin for producing monosaccharides, as well as the combination of such chemical hydrolysis with enzymatic hydrolysis using enzymes with amylolytic activity ("amyl glucosidases") to obtain monosaccharides from chitin and/or chitosan. The process allows the monomer (the monosaccharide) to be obtained directly from the chitosan and/or chitin unlike previously developed processes which produced oligomers.

While mineral acids such as HCl and/or short chain carboxylic acid (such as acetic acid) under mild conditions induce depolymerization with formation of oligomers, it was noted that the acid medium containing acetic acid under vigorous conditions (high concentrations of nitrous acid) in the depolymerization reaction of chitosan in acetic acid is capable of producing monosaccharides (changes in such conditions, such as the change of the chemical species used to acidify the reaction medium or variations in nitrous acid concentration, can generate different products).

Similarly, the combination of chemical hydrolysis with nitrous acid, i.e., depolymerization of chitin and/or chitosan with nitrous acid followed by enzymatic hydrolysis with enzymes having amylolytic activity (which are able to promote the depolymerization of oligomers produced in chemical hydrolysis with nitrous acid) also produces monosaccharides.

The production of monosaccharides described herein can be exploited by the sugar industry and sugar derivatives industry, including bioethanol and hydroxymethylfurfural, which is the precursor of several chemical compounds and has the advantage of being used as a raw material a widely available, renewable and abundant biomass. The process is fast and simple to perform, and the reagents used are low cost.

BRIEF DESCRIPTION OF THE DRAWINGS

Many aspects of the disclosure can be better understood with reference to the following drawing, wherein FIG. 1 is a mass spectrometer plot of the presence of monosaccharide over time.

Production Methodology

For acid hydrolysis reaction, 10.00 g of chitin or chitosan were mixed in 500.0 mL of acetic acid (CH3COOH) (2%) under constant stirring. Subsequently, 100.0 mL of a 0.66 mol/L sodium nitrite (NaNO2) solution (for in situ formation of nitrous acid) was added and heated at mild temperature (35° C. to 55° C.) for 3 minutes. The final product is a yellowish suspension with low viscosity.

For the combined hydrolysis (chemical and enzymatic), the chemical hydrolysis described in the previous paragraph was conducted in a sample of chitin (shredded crustacean exoskeleton, such as shrimp exoskeleton—Decapoda crustaceans) followed by the hydrolysis with an amyl glucosidase enzyme (an enzyme with amylolytic activity) under optimum pH and enzyme temperature conditions (pH≈5.0 and T≈52° C.). As in the chemical hydrolysis, the product is also a yellow and low viscosity suspension containing the monosaccharide (the sugar).

The isolation of fermentable hexoses present in the product for characterization was performed according to Ascencio [Ascencio, S. D. Extraction, quantification and chemical characterization of low molecular mass carbohydrates of red algae (*Rhodophyta*). Curitiba, 2002. Dissertation (Master in Biochemistry)—Biological Sciences, Federal University of Paraná. 100 p, 2002. Advisor: Prof. Dr. Miguel Daniel Noseda] by gel filtration chromatography using a glass column (50×1.5 cm d.i.) containing BioGel P-2 (exclusion range: 1800-100 Daltons) with total volume ($V_t$) of 88 mL and void volume ($V_0$) of 60 mL. The total volume of the column was measured by the addition of water in the column to the level determined to be filled by the gel, with the eluent being deionized water (pH 6.51).

Fractions of 10 mL of the filtrate were collected every 15 minutes through Spectrum Labs CF-2 fraction collector for 9 hours. The initial technique used for chromatographic screening was thin layer chromatography (TLC), as described by WAKSMUNDZKA-HAJNOS, M.; SHERMA, J.; KOWALSKA, T. Thin Layer Chromatography in Phytochemistry. Chromatographic Science Series: 99, 2008, consisted in using silica gel 60 sheets (ALUGRAM®); previously activated, 110° C. for 30 minutes; used as stationary phase. The different samples were applied in the lower part, in different spots, in a 2.5 cm line above the beginning of the sheet, by means of glass capillaries. After this, the base of the sheet was immersed in the mobile phase, in a chromatographic vessel, and the run occurred until the mobile phase reached the maximum height stipulated (2.5 cm below the end of the sheet).

The mobile phase used in this analysis consisted of: ethyl acetate:isopropyl alcohol:acetic acid:distilled and deionized water (4:2:2:1). The development was performed at 100° C. until the desired coloration was reached (about 5 minutes). The developer consisted of 250 mg of orcinol, solubilized in 95 ml of ethanol and 5 ml of sulfuric acid, which was sprinkled on the plate before it was brought to the stove. The standard used was glucose. All reagents used, as well as the standard, present high purity levels.

After the initial screening by thin layer chromatography (TLC), the fractions identified with sugars were sent for HPLC analysis. Due to the use of the refractive index detector (RID) instead of UV-VIS detection, it was not necessary to modify the carbohydrate molecules by derivatization.

It was used a Shimadzu high performance liquid chromatograph (LC-10 Series Avp; degasser: DGU-14A, integrator: CLASS LC-10), isocratically eluted by pumping (LC-10AD) a mobile phase composed of 5 mM sulfuric acid in ultrapure water (distilled and deionized). The eluent flow was 0.6 mL/min at 30° C. (CTO-10A column furnace), with total run time of 20 minutes. Detection occurred in refractive index detector (Shimadzu, model RID-10A). An aliquot of 20.0 µl of the sample was manually injected (Rheodyne injector, 20 mesh) and permeated by a Phenomenex Rezex ROA-Organic Acid H+column (300×7.8 mm) with direct connection to Phenomenex Carbo-H safety cartridge (4×3 mm) filled with a material similar to the material of the main column. In the sample of flask 9, shown in FIG. 1, it was possible to identify the presence of hexose. The technique allowed to reveal the presence of the monosaccharide at the same time of glucose retention, as can be seen in FIG. 1, indicating the presence of sugar in the sample.

The sample was also characterized by a gas chromatograph coupled to a Saturn mass spectrometer, 4000 model, equipped with a Factor Four Capillary Column VF-1 ms column (30 m×0.25 mm×0.25 µm). The initial temperature was 50° C., gradually increasing (flow of 40° C. per minute) until 220° C., analysis temperature of the alditol acetates. The temperature remained constant during the analysis time (25 minutes). The entrainment gas used was helium, with a flow rate of 1 mL/min. The areas of the peaks of interest were determined by integration with the Varian WS software, and the mass fragments were obtained by electron impact at 70 meV, whose values can be observed in the mass spectrum. The analysis was performed by comparing retention times and fragmentation profiles of the samples and the patterns.

Finally, 1D and 2D nuclear magnetic resonance analyzes were carried out on a Bruker Avance DRX400 (BrukerGermany) spectrometer, at a base frequency of 400 MHz (1H) and 100 MHz (13C), and a Bruker Avance III 600 spectrometer (BrukerGermany), with base frequencies of 150 MHz (13C) and 600 MHz (1H). Analysis temperatures ranged from 30 to 50° C. The samples were solubilized in 99% D2O at a concentration of 80 mg/mL for 13C and 20 mg/mL for 1H and 2D analyzes (HSQC) and placed in 5 mm OD tubes. The chemical shifts, expressed in ppm, were determined using acetone as the internal standard for both 13C (30.20 ppm) and 1H (2.224 ppm) analyzes, which revealed the presence of the glucose-like hexose with a compatible profile at anhydromanose.

DESCRIPTION OF THE INVENTION

In this invention, we report the observation of an effective chitin or chitosan depolymerization in fermentable monosaccharides through the combined use of nitrous acid with high yields in the conversion of biomass to monosaccharides. Alternatively, the procedure also shows efficiency when used combinations of enzymatic hydrolysis of chitin or chitosan with the use of enzymes with amylolytic activity combined with the chemical hydrolysis described above.

Example 1

Prepare a 1-5% (mass/volume) chitin or chitosan solution in acetic acid solution (1-5%) under stirring at room temperature for an appropriate time (1-30 minutes). Then, a freshly made concentrated sodium nitrite (NaNO2) solution (0.5 to 5 mol/L) is added to the solution (5-50% of the volume of the solution) (nitrite tends to oxidize to nitrate, thus, using an old made solution reduces the efficiency of the process) under stirring at room temperature. The reaction produces nitrogen gas which can be observed by the vigorous gas release.

Example 2

Prepare the chitin or chitosan solution according to example 1 by changing the heating of the mixture while stirring for mild heating (30° C. to 55° C.). The temperature accelerates the reaction reducing the total time to obtain the product.

Example 3

Prepare the chitin or chitosan solution according to example 1 by changing the heating of the mixture while stirring for intense heating (55° C.-99° C.).

Example 4

Prepare a 1-5% (mass/volume) chitin or chitosan solution in acetic acid solution (1-5%) with rapid stirring at room temperature for an appropriate time (1 second to 59 seconds). Add a freshly made concentrated sodium nitrite (NaNO2) solution (0.5 to 5 mol/L) without stirring and store the mixture for longer than 30 minutes. The reaction usually proceeds by obtaining glucose in solution.

Example 5

Prepare the mixture according to example 4 with mild heating (30° C.-55° C.) during the preparation of the chitosan mixture with acetic acid and the addition of sodium nitrite solution.

Example 6

Prepare the mixture according to example 4 with intense heating (55° C.-100° C.) during the preparation of the chitosan mixture with acetic acid and addition of sodium nitrite solution.

Example 7

Prepare a mixture of chitin or chitosan in short chain organic acids or in mineral acids with concentration ranging from 1-20%. Then add concentrated or diluted sodium nitrite solution (NaNO2) under heating (above 30° C.) and stirring or at rest. Subsequently, add the enzyme with amylolytic activity under suitable pH and temperature conditions (for enzymatic activity) under stirring or at rest for a sufficient period of time to optimize yield.

Example 8

Prepare a mixture of chitin or chitosan according to example 7. Then add concentrated or diluted sodium nitrite solution at room temperature under stirring or at rest. Soon after adding the enzyme with amylolytic activity under pH and temperatures conditions suitable for the enzymatic activity under stirring or at rest for a sufficient period of time for optimization of yield.

Example 9

Prepare a chitin or chitosan mixture according to example 7. Add the enzyme having amylolytic activity under suitable pH and temperature conditions (for optimum activity of the enzyme) under stirring or at rest for a sufficient period of time for optimization of yield. Immediately after adding concentrated or diluted sodium nitrite solution (NaNO2) under heating (temperature above 30° C.) and stirring or at rest.

Example 10

Prepare a chitin or chitosan mixture according to example 7. Add the enzyme having amylolytic activity under suitable pH and temperatures conditions for the enzymatic activity under stirring or at rest for a sufficient period of time to optimize the yield. Next, add concentrated or diluted sodium nitrite solution at room temperature under stirring or at rest.

Example 11

Prepare the chitin or chitosan solution according to example 1 by changing the use of alternative forms of nitrous acid such as the saturation of the reaction medium with nitrogen oxides such as dinitrogen tetroxide, N2O4, dinitrogen pentoxide, N2O5, and others, to obtain nitrous acid in the reaction solvent followed by the modifications described in examples 2, 3, 4, 5, 6, 7, 8, 9 and 10.

The invention claimed is:
1. A process for producing a monosaccharide from chitin and/or chitosan comprising the following steps:
 (a) preparing a solution containing 1 to 5 volume % of chitosan and/or chitin in acetic acid with stirring for 1 to 30 minutes;
 (b) adding nitrous acid in an amount of 5 to 50 volume % to the solution prepared in step (a) wherein the nitrous acid is produced in situ by adding sodium nitrite solution to the solution prepared in step (a) in a concentration from 0.5 to 5 mol/L, or by saturation of the solution prepared in step (a) with gaseous nitrogen oxides under stirring and heating; and
 (c) adding an enzyme having amylolytic activity to the solution prepared in step (b), or between steps (a) and (b), whereby to directly produce the monosaccharide without producing oligomers, wherein the enzyme having amylolytic activity is an amyl glucosidase, and the monosaccharide produced is anhydromannose.
2. The process according to claim 1, wherein step (a) is conducted while heating at a temperature between 30° C. to 55° C.
3. The process according to claim 1, wherein, step (b) is conducted while stirring and heating for one minute to 72 hours.
4. The process according to claim 1, wherein step (b) is conducted while heating at a temperature of 55° C. to 100° C.
5. The process according to claim 2, wherein, in step (b) stirring and heating is continued for one minute to 72 hours.
6. The process according to claim 2, wherein step (b) is conducted while heating is at a temperature of 55° C. to 100° C.
7. The process according to claim 3, wherein step (b) is conducted while heating is at a temperature of 55° C. to 100° C.

8. The process according to claim 1, wherein said enzyme having amylolytic activity is added to the solution between steps (a) and (b) with stirring or at rest.

9. A process for producing a monosaccharides from chitin and/or chitosan, the process comprising the following steps:
   (a) preparing a solution containing 1 to 5 volume % of chitosan and/or chitin in a mineral acid having a concentration of 1 to 20 volume % with stirring for 1 to 30 minutes;
   (b) adding nitrous acid in an amount of 5 to 50 volume % to the solution prepared in step (a) wherein the nitrous acid is produced in situ by adding sodium nitrite solution to the solution prepared in step (a) in a concentration from 0.5 to 5 mol/L, or by saturation of the solution prepared in step (a) with gaseous nitrogen oxides under stirring and heating; and
   (c) adding an enzyme having amylolytic activity to the solution prepared in step (b), or between steps (a) and (b), whereby to directly produce the monosaccharide without producing oligomers, wherein the enzyme having amylolytic activity is an amyl glucosidase, and the monosaccharide produced is anhydromannose.

10. The process according to claim 9, wherein step (a) is conducted by heating at a temperature between 30° C. to 55° C.

11. The process according to claim 9, wherein, step (b) is conducted while stirring and heating for one minute to 72 hours.

12. The process according to claim 9, wherein step (b) is conducted while heating at a temperature of 55° C. to 100° C.

13. The process according to claim 10, wherein, step (b) stirring and heating is continued for one minute to 72 hours.

14. The process according to claim 10, wherein step (b) is conducted heating while at a temperature of 55° C. to 100° C.

15. The process according to claim 11, wherein step (b) is conducted heating while at a temperature of 55° C. to 100° C.

16. The process according to claim 9, wherein said enzyme having amylolytic activity is added to the solution between steps (a) and (b) with stirring or at rest.

* * * * *